(12) United States Patent
Winston et al.

(10) Patent No.: US 6,842,639 B1
(45) Date of Patent: Jan. 11, 2005

(54) METHOD AND APPARATUS FOR DETERMINING NEOVASCULAR FLOW THROUGH TISSUE IN A VESSEL

(75) Inventors: Thomas R. Winston, Leawood, KS (US); John M. Neet, Lawrence, KS (US); Nicholas Wolfe, Olathe, KS (US)

(73) Assignee: Intraluminal Therapeutics, Inc., Carlsbad, CA (US)

( * ) Notice: Subject to any disclaimer, the term of this patent is extended or adjusted under 35 U.S.C. 154(b) by 0 days.

(21) Appl. No.: 09/539,015

(22) Filed: Mar. 30, 2000

Related U.S. Application Data

(63) Continuation-in-part of application No. 09/060,487, filed on Apr. 15, 1998, now Pat. No. 6,193,676, which is a continuation-in-part of application No. 08/943,386, filed on Oct. 3, 1997, now Pat. No. 5,951,482.

(51) Int. Cl.[7] .............................................. A61B 5/00
(52) U.S. Cl. ...................... 600/478; 600/479; 600/505; 356/477
(58) Field of Search ............................... 600/342, 476, 600/478, 479, 487, 505, 585; 356/477, 345; 606/2, 3, 15

(56) References Cited

U.S. PATENT DOCUMENTS

| 4,575,246 | A | * | 3/1986 | Nishizawa et al. | ......... 356/346 |
|---|---|---|---|---|---|
| 5,459,570 | A | * | 10/1995 | Swanson et al. | ............. 356/345 |
| 5,549,114 | A | * | 8/1996 | Petersen et al. | ............. 600/504 |
| 5,582,171 | A | * | 12/1996 | Chornenky et al. | ......... 600/425 |
| 5,951,482 | A | * | 9/1999 | Winston et al. | ............. 600/476 |
| 6,006,128 | A | * | 12/1999 | Izatt et al. | .................. 600/476 |
| 6,013,072 | A | * | 1/2000 | Winston et al. | ................ 606/15 |
| 6,063,093 | A | * | 5/2000 | Winston et al. | ............. 606/108 |
| 6,134,003 | A | * | 10/2000 | Tearney et al. | ............. 356/345 |
| 6,179,611 | B1 | * | 1/2001 | Everett et al. | ................ 433/29 |
| 6,193,676 | B1 | * | 2/2001 | Winston et al. | ............. 500/585 |
| 6,485,413 | B1 | * | 11/2002 | Boppart et al. | ............. 600/160 |

* cited by examiner

*Primary Examiner*—Ruth S. Smith
(74) *Attorney, Agent, or Firm*—Armstrong Teasdale LLP

(57) ABSTRACT

Methods and apparatus for guiding a guide wire through a blood vessel are described. An exemplary embodiment includes a guide wire coupled to an interferometric guidance system. The interferometric guidance system is configured to provide imaging information of the vessel. The guidance system further includes a flow detection circuit for performing Doppler shift analysis to determine the presence of neovascular channels through an obstruction in the vessel. The neovascular fow information is used by the guide wire operator to guide the guide wire through the obstruction.

18 Claims, 5 Drawing Sheets

METHOD AND APPARATUS FOR DETERMINING NEOVASCULAR FLOW THROUGH TISSUE IN A VESSEL

This application is a continuation in part of U.S. Ser. No. 09/060,487 filed Apr. 15, 1998 now U.S. Pat. No. 6,193,676 which is a continuation in part of U.S. Ser. No. 08/943,386 filed Oct. 3, 1997 now U.S. Pat. No. 5,951,482.

BACKGROUND OF THE INVENTION

This invention relates generally to medical guide wires and catheters and more particularly, to guiding assemblies and guiding methods for guide wires.

Disease processes, e.g., tumors, inflammation of lymph nodes, and plaque build-up in arteries, often afflict the human body. As one specific example, atherosclerotic plaque is known to build up in the walls of arteries in the human body. Such plaque build-up restricts circulation and often causes cardiovascular problems, especially when the build-up occurs in coronary arteries.

To treat such disease, it often is necessary to guide a medical device to the diseased site, and then use the medical device to treat the diseased area. Often a guide wire is used to help guide other treatment devices. A guide wire typically is required to properly position a catheter in an artery. The guide wire is advanced and forms a path, through the artery and region of plaque build-up. The catheter or other device such as a balloon or rotational atherectomy device is then guided through the artery using the guide wire.

Known guide wires exist for the treatment of tissue. For example, known guide wires use laser energy to remove plaque build-up on artery walls as the guide wire is advanced. One known catheter includes a laser source and a guide wire body. The guide wire body has a first end and a second end, or head, and several optic fibers extend between the first end and the second end. The laser source is coupled to each of the optic fibers adjacent the catheter body first end and is configured to transmit laser energy simultaneously through the optic fibers.

To remove arterial plaque, for example, the guide wire body is positioned in the artery so that the second end of the guide wire body is adjacent a region of plaque build-up. The laser source is then energized so that laser energy travels through each of the optic fibers and substantially photoablates the plaque adjacent the second end of the catheter body. The guide wire body is then advanced through the region to photoablate the plaque in the entire region.

However, it often is difficult to guide known guide wires through the body without risking damage. For example, known guide wires typically cannot be easily advanced through partially or totally occluded arteries without substantial risk of damaging or puncturing the artery wall. As the guide wire is advanced through the artery, it will encounter obstructions to advancement including plaque build-up or the artery wall itself. However, known guide wires typically do not distinguish between plaque build-up and the artery wall. An operator may therefore incorrectly identify an obstruction as plaque build-up and attempt to push the guide wire through the obstruction, resulting in injury or puncture of the artery wall.

Arteries that become totally occluded will, over time, develop neovascular channels (microchannels) that allow blood to flow through the occlusion from the proximal side to the distal end of the lesion. These neovascular channels often offer a path of least resistance for an interventional procedure. However, known guide wire guiding methods and apparatus do not detect the presence of neovascular channels when they exist. In particular, these neovascular channels are not visible under x-ray angiography. Thus, operators of guide wires are limited in their ability to take advantage of the existence of channels in advancing the guide wire.

Accordingly, it would be desirable to provide a guide wire including a guidance system to determine the safety of advancing the guide wire further into the vessel. In particular, it would also be desirable to provide such a guide wire with the capability of providing information to an operator to distinguish among the types of obstructions which might be hindering advancement of the guide wire. It would be further desirable to detect the presence of neovascular channels through an obstruction, to identify a path from the proximal to the distal end of the obstruction.

BRIEF SUMMARY OF THE INVENTION

In an exemplary embodiment, methods and apparatus for guiding a guide wire include an interferometric guidance system that determines the presence of neovascular channels. Particularly, the guide wire assembly includes a substantially cylindrical guide wire including a first end, a second end or distal end (guide wire head), and a bore extending between the first and second ends. The interferometric guidance system is coupled to the guide wire and includes a low coherent illumination source, an optical beam splitter, a first optic fiber, a second optic fiber, a detecting element including a photodetector and a computer. The first optic fiber is wrapped around a first piezo electric transducer (PZT), and the second optic fiber is wrapped around a second PZT. The first PZT and second PZT are connected to the guidance system in reverse parallel configuration so that when a sawtooth, triangular, or some other pattern of voltage signal is applied, one PZT expands while the other PZT contracts. The first optic fiber includes a first end and a second end, and extends through the guide wire bore so that the second end is adjacent the guide wire second end. The second optic fiber of the guidance system similarly includes a first end and a second end, and a fixed reflector, such as a metal deposit reflector, on the second optic fiber second end.

The beam splitter includes an illumination source input, a first beam output, a second beam output, and a combined beam output. The illumination source is coupled to the illumination input of the beam splitter. The first end of the first optic fiber, and the first end of the second optic fiber are coupled to the beam splitter. Particularly, the first optic fiber first end is communicatively coupled to the first beam output of the beam splitter, and the second optic fiber first end is communicatively coupled to the second beam output of the beam splitter. The beam splitter combined beam output is coupled to the photodetector, which is communicatively coupled with the computer. The photodetector is configured to determine interference between substantially equal reflected light beams which are initially emitted from the same source and are later split to propagate separately through the first optic fiber and through the second optic fiber. Particularly, the photodetector processes interferometric information that is generated from light reflected from blood flowing in a vessel being treated.

In an exemplary embodiment, the guide wire guiding apparatus also includes a neurovascular flow detection circuit. In one embodiment the detecting element includes the flow detection circuit. The circuit is configured to detect the Doppler shift change in frequency of the light reflected from target tissue. The Doppler shift information detects the presence of neovascular channels through an obstruction, by revealing relative changes in blood flow velocity at the guide wire distal end. The Doppler shift results from two components. More specifically, a known component of the Doppler shift is due to the stretching and contraction of the optical fiber with the PZT's. A second, variable component of the Doppler shift is due to the velocity of the target from which light is reflected. The first component of the shift is determined by the operating characteristics of the PZT and the applied voltage profile. Thus, the first component of the overall Doppler shift is predicted by the path-length change (velocity) and the wavelength of the light. The actual Doppler shift is measured by passing the signal from the photodetector through a broadband filter and then to a frequency-to-voltage converter. The difference between the actual Doppler shift and the predicted Doppler shift of the path-length change indicates the velocity of the reflecting target, which in this case is blood. The direction of blood flow is also determined by the relative difference between the actual Doppler shift and the path-length change component. More specifically, the direction of blood flow is determined by determining whether the actual Doppler shift is more or less than the path-length change component.

The Doppler shift information indicating relative flow is displayed to the operator by a visual graphic display. Alternatively, the relative flow is communicated to the operator using a tone generator to generate an audible tone. The apparatus and methods thus indicate relative blood flow, or changes in blood flow. The operator then uses the blood flow information to locate regions of maximum blood flow or minimum flow, depending on the specific application.

In operation, the guide wire head is inserted at least partially into, for example, a blood vessel so that the guide wire head and the first optic fiber second end of the guidance system is positioned outside the blood vessel. The beam splitter splits the illumination source light beam into two beams. The first beam is transmitted through the first optic fiber to the tissue located in front of the second end of the guide wire. The tissue, acting as a reflective surface, reflects at least a portion of the first light beam back into the first optic fiber and back to the beam splitter. The second light beam is transmitted through the second optic fiber to the fixed reflector which reflects the second light beam, and the reflected beam is returned to the beam splitter. The beam splitter combines the reflected first and second light beams, resulting in constructive or destructive interference of the two light beams, and creates a combined light beam output. The combined light beam output, including interference information, is coupled to the detecting element. The detecting element output is processed by the computer and visually displayed or otherwise communicated to the operator to navigate the guide wire second end further into the vessel, and through an obstruction.

Prior to advancing the guide wire further into the vessel, out of phase frequency signals are applied to the PZTs, causing the PZTs to alternately expand and contract out of phase with one another. This action alternately stretches each optic fiber to extend its length. Specifically, alternating between extending the length of the first optic fiber and extending the length of the second optic fiber changes the optical path-lengths for the first and second light beams. This shifts the interference point of the reflected first and second light beams, producing the interference data which is processed by the detecting element to provide information regarding the tissue at known distances from the guide wire second end. The flow detection circuit provides information regarding the relative blood flow at the guide wire second end. This blood flow information indicates the presence of neovascular channels, thus aiding the operator in identifying a suitable path for advancing the guide wire through an obstruction. Both the interference information and blood flow information are visually displayed or otherwise communicated to the operator as the guide wire is advanced, so that the operator is guided in navigating and advancing the guide wire.

BRIEF DESCRIPTION OF THE DRAWINGS

FIG. 8 is an exemplary visual graphic display of intensity of reflected light versus distance for an operator of the guide wire guiding apparatus.

DETAILED DESCRIPTION OF THE INVENTION

Figure 1:
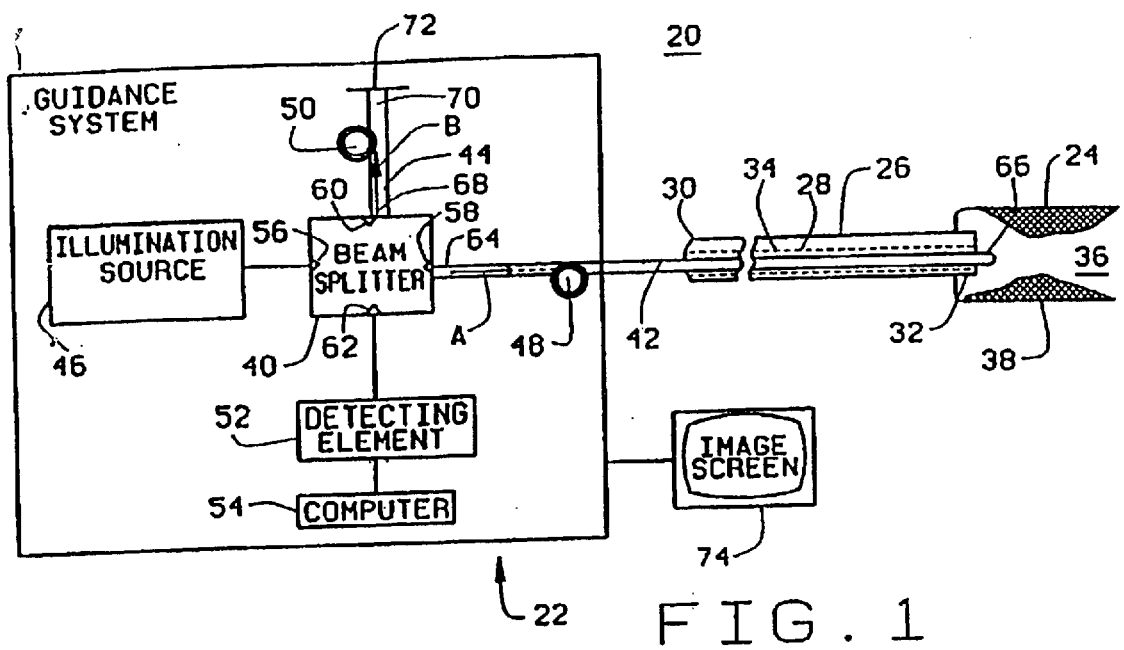
FIG. 1 is a pictorial illustration of a guide wire guiding apparatus in accordance with one embodiment of the present invention inserted into a blood vessel.

FIG. 1 is a pictorial illustration of a guide wire apparatus 20 in accordance with one embodiment of the present invention. Guide wire apparatus 20 includes an interferometric guidance system 22 and is configured to be inserted into a body passage 24 such as a blood vessel. In an exemplary embodiment, interferometric guidance system 22 includes a circuit for detecting neovascular flow, as described in detail below. Guide wire assembly 20 further includes a catheter 26 extending over a guide wire 28. Guide wire 28 has a first end 30 and a head 32, and includes a bore 34 extending between first end 30 and head 32. Guide wire second end 32 is positioned within an interior 36 of blood vessel 24 adjacent tissue through which guide wire 28 is to be advanced, e.g., plaque 38. Guide wire 28 is formed, for example, with a coiled wire.

Guidance system 22 includes a beam splitter 40, a first, or measuring, optic fiber 42, and a second, or reference, optic fiber 44, an illumination source 46, two piezo electric transducers (PZT's) 48 and 50, a detecting element 52, and a computer 54. Beam splitter 40 includes an illumination source input 56, a first beam output 58, a second beam output 60, and a combined beam output 62. First optic fiber 42 includes a first end 64 and a second end 66, and is coupled to guide wire 28 so that second end 66 is adjacent guide wire head 32 and is positioned in blood vessel interior 36. First optic fiber first end 64 second end 66 is glued to guide wire head 32, for example with epoxy and a portion of second end 66 extends beyond guide wire head 32 as shown. Second optic fiber 44 also includes a first end 68 and a second end 70. Second optic fiber second end 70 includes a fixed reflector 72. First optic fiber first end 64 is coupled to first beam output 58, and second optic fiber first end 68 is coupled to second beam output 60. First optic fiber 42 is configured to emit energy waves substantially coaxially with respect to guide wire head 32. In one embodiment, illumination source 46 is a low coherent illumination source, for example, a laser, edge-emitting light emitting diode (ELED) or superluminescent emitting diode (SLD).

Optic fibers 42 and 44 are fabricated from drawn or extruded glass or plastic having a central core and a cladding of a lower refractive index material to promote internal reflection. In one embodiment, optic fibers 42 and 44 are polarization-preserving optic fibers which preserve the plane of polarization of a light beam as it propagates along the length of a fiber. Polarization-preserving optic fibers maintain the polarization of the light beam by having asymmetry in the fiber structure, either in the overall shape of the fiber, or in the configuration of the cladding with respect to the central core. In one embodiment, the diameter of each fiber is about 80 microns to about 125 nm microns, but the diameter may vary.

PZT's 48 and 50 are fabricated from piezoelectric material wrapped around a cylinder, and are connected in guidance system 22 in reverse parallel configuration so that one PZT expands while the other contracts. PZT's 48 and 50 are configured so that expansion and contraction of the piezoelectric material changes the diameter of the PZT's. First optic fiber 42 and second optic fiber 44 are wrapped uniformly in layers around PZT's 48 and 50. In one embodiment, first optic fiber 42 is wrapped approximately 100 times around PZT 48, and second optic fiber 44 is wrapped approximately 100 times around PZT 50. The length of each optic fiber does not exceed about 110 meters. PZT's 48 and 50 are each configured to expand and contract, thereby changing in diameter, upon application of a voltage signal, for example, a triangular or a sawtooth wave. In one embodiment, the voltage signal has a voltage of about 1 kV or below, and a frequency of about 10 hertz to about 30 hertz, with a current of less than 100 milliamps, although other voltage signal values may be used. In alternate embodiments, PZTs 48 and 50 are instead other materials which expand and contract to alter the length of first optic fiber 42 and second optic fiber 44.

In one embodiment, detecting element 52 is a photodetector coupled to an image screen 74 and configured to transmit data to image screen 74. Particularly, detecting element 52 is configured to determine interference between a light beam propagating through first optic fiber 42 and a light beam propagating through second optic fiber 44, and to generate interference data representative of such interference. For example, in one embodiment detecting element 52 includes a detector, a demodulator and an analog digitizer cooperating to generate the interference data. The interference data is transmitted to computer 54 which generates image data for display on image screen 74, or to notify an operator operating by hand of an adverse situation and to discontinue pursuing the current direction of advancement.

Figure 2:
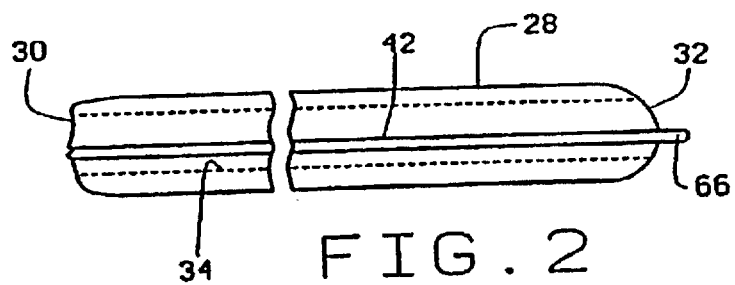
FIG. 2 is a sectional view of the guide wire shown in FIG. 1.

FIG. 2 is a sectional view of the guide wire. Guide wire 28 includes guide wire bore 34 extending between guide wire first and second ends 30 and 32, respectively. First optic fiber 42 extends through guide wire bore 34 so that second end 66 of first optic fiber 42 is adjacent guide wire second end 32. In one embodiment, first optic fiber second end 66 is flat polished. In an alternative embodiment, second end 66 is polished at a small angle, about 6 to about 10 degrees, relative to a cross-sectional plane orthonormal to the long axis of the optic fiber, to reduce reflections at the interface between second end 66 and tissue. In an exemplary embodiment the angle of the second end is about 8 degrees. In an exemplary embodiment, guide wire bore 34 has a diameter of approximately 0.010 inches. First and second optic fibers 42 and 44 have, for example, respective diameters of approximately 0.007 inches.

Figure 3:
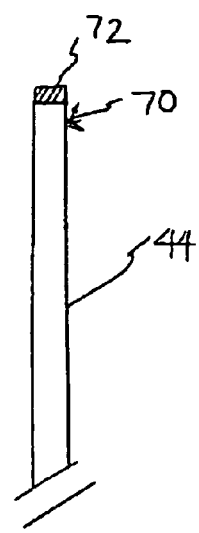
FIG. 3 is a schematic illustration of a fixed reflector on the second optic fiber.
Figure 4:
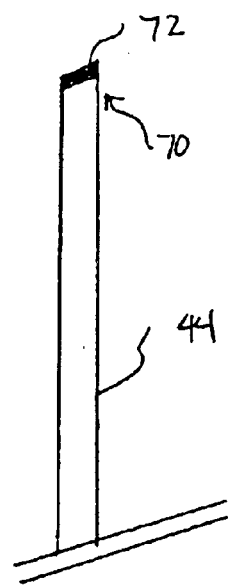
FIG. 4 is a schematic illustration of an alternative fixed reflector on the second optic fiber.

FIG. 3 is a schematic illustration of a fixed reflector 72 on second optic fiber second end 70. In one embodiment as shown in FIG. 3, second optic fiber second end 70 is polished flat. FIG. 4 is a schematic illustration of an alternative embodiment in which second optic fiber second end 70 is polished at a small angle (of about 6 to about 10 degrees, and in an exemplary embodiment about 8 degrees) relative to a cross-sectional plane orthonormal to the long axis of the optic fiber. In either case, fixed reflector 72 is fabricated by depositing gold onto second optic fiber end 70 using known depositing methods. In alternate embodiments, fixed reflector 72 is fabricated from any material having a different refractive index than second optic fiber 44, or from another type of mirror. Noble metals such as gold, platinum and silver are inert, yield good reflections and are therefore especially suitable for reflector 72, but other suitable materials are known and used.

Figure 5:
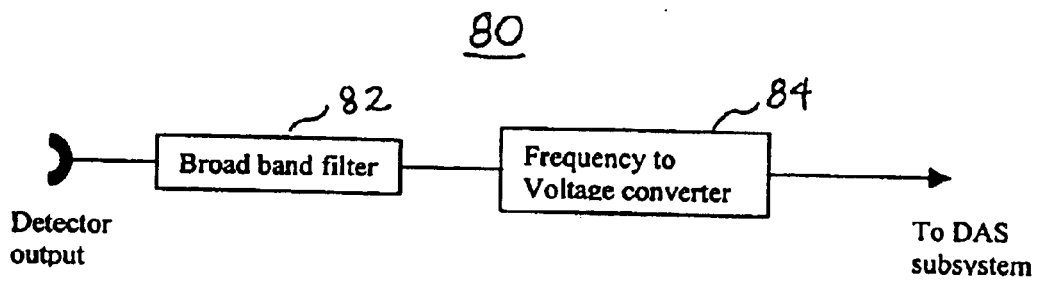
FIG. 5 is a block diagram illustrating a flow detection circuit in the guide wire guiding apparatus.

FIG. 5 is a block diagram illustrating an exemplary flow detection circuit 80 in the guide wire apparatus. In an exemplary embodiment, the guide wire apparatus includes flow detection circuit 80 for determining blood flow relative second 32 of guide wire. The blood flow information is used by the operator to detect the presence of neovascular channels through an obstruction in a vessel. The blood to the imaging produced by the interferometric information as described above. Alternative embodiments include those in which only blood flow information is generated and used.

In one embodiment, flow detection circuit 80 is coupled to the circuit in detecting element 52, in parallel to the demodulator in detecting element 52 as described above. Flow detection circuit 80 includes a broad band filter 82 coupled to a frequency-to-voltage converter 84 having an output to a data acquisition subsystem (DAS). In the exemplary embodiment, flow detection circuit 80 operates on a frequency modulated signal to detect variances in the Doppler shift due to changes in velocity of blood flow in the blood vessel under examination. More specifically changes in the velocity of blood flow relative to guide wire second end 32, produce a Doppler shift in the scanning frequencies, resulting in a frequency-modulated signal centered on a carrier frequency. The frequency shift is detected by filter 82 and, converted by frequency-to-voltage converter 84 to a voltage signal proportional to the frequency shift. For example, converter 84 includes circuitry to convert frequency shifts indicative of blood flow in one direction (relative to guide wire second end 32) to a proportionally negative voltage signal. Similarly, frequency shifts indicative of blood flow in the opposite direction are converted to a proportionally positive voltage signal. In an alternative embodiment, the converter 84 includes circuitry for offsetting the frequency shift in one direction so that the absolute value of the frequency shift is obtained. Thus, frequency shifts indicating both directions of blood flow are converted to a unipolar voltage signal.

Figure 6:
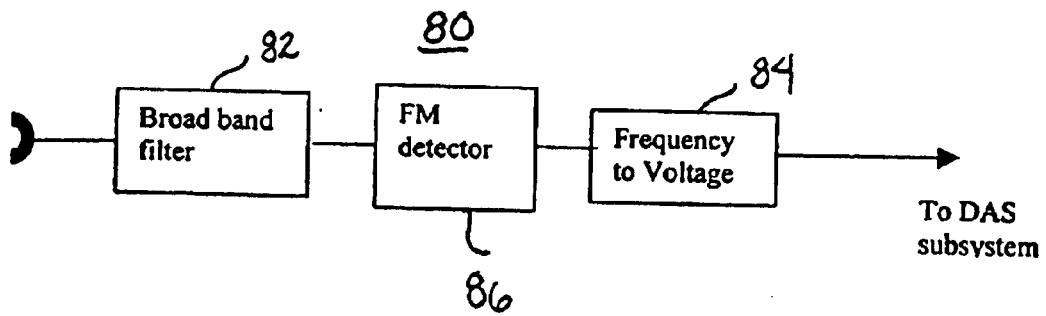
FIG. 6 is a block diagram illustrating an alternative embodiment of the flow detection circuit in FIG. 4.

FIG. 6 is a block diagram of an alternative flow detection circuit 80. In this embodiment, circuit 80 includes an FM detector 86 between the output of broadband filter 82 and the input to frequency-to-voltage converter 84. The addition of FM detector 86 increases the sensitivity of circuit 80 to the Doppler frequency shifts.

Figure 7:
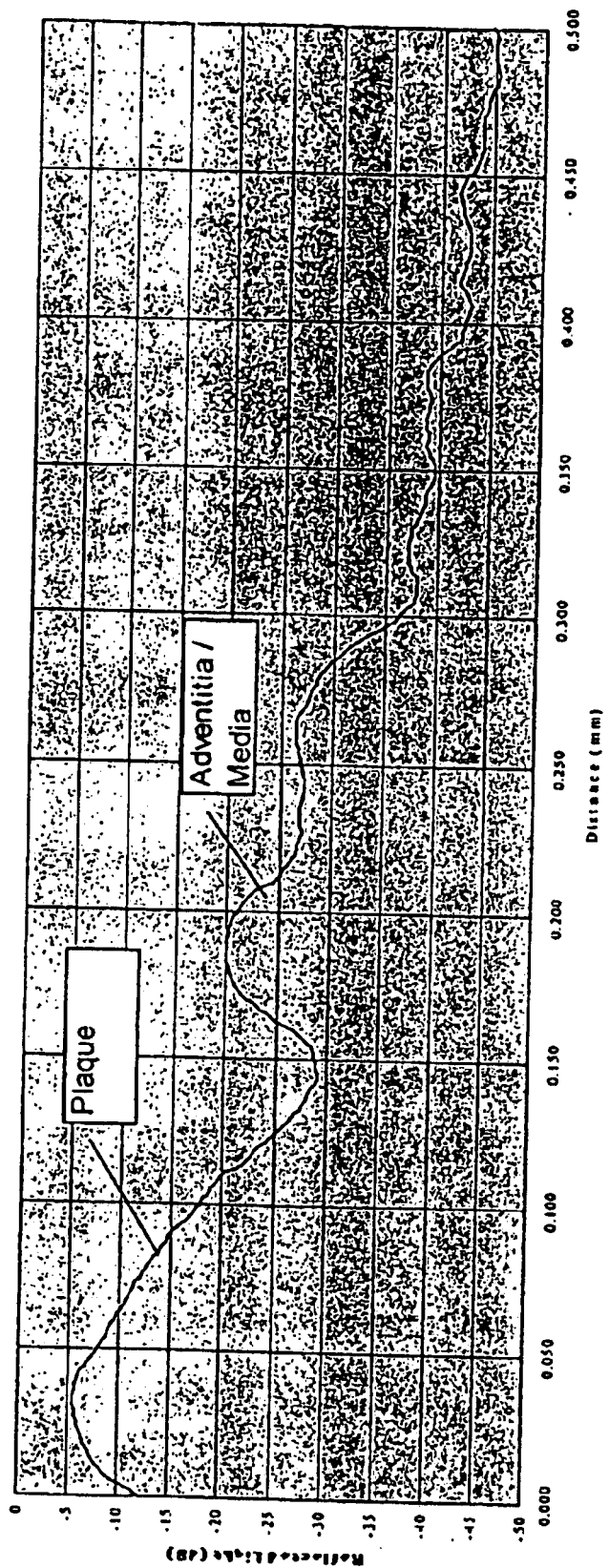
FIG. 7 is an exemplary graph of intensity of reflected light versus distance, as determined by the guide wire guiding apparatus.
Figure 6:
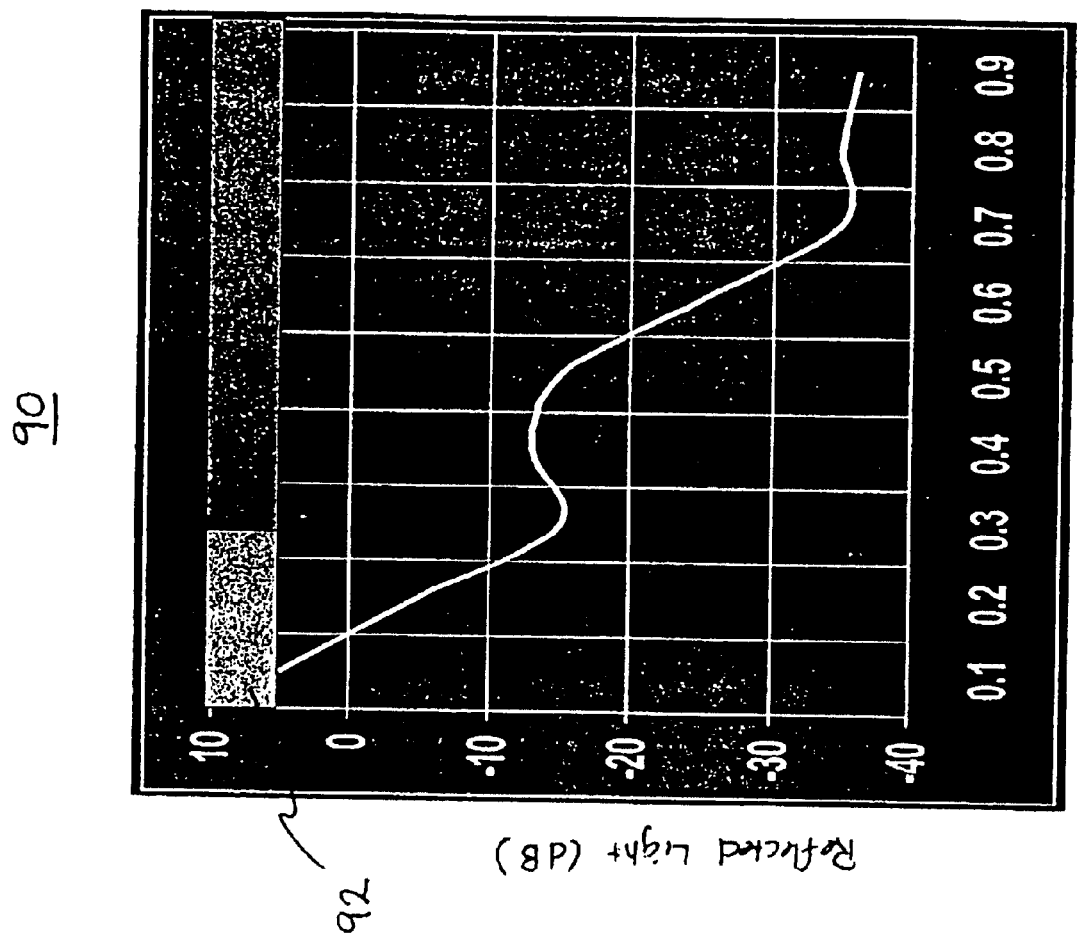

Referring again to the interferometric imaging information, FIG. 7 is an exemplary graph of intensity of light reflected from tissue being examined, versus the distance from a predetermined point. The predetermined point is, for example, the second end 32 of the guide wire. As shown in FIG. 7, experimental evidence shows that, in a blood vessel, there is a predictable change in the reflected light intensity versus distance profile when the normal vessel (e.g. arterial) tissues (media and adventitia) are in the field of view. Using this relationship of reflected light intensity to distance from a predetermined point, a simple slope detection algorithm as previously described is used to determine the distance from second end 32 of the guide wire to the normal arterial wall. The distance information is obtained and displayed as a visual graphic display on a computer video monitor.

FIG. 8 is an exemplary visual graphic display 90 of intensity of reflected light versus distance for an operator of the guide wire guiding apparatus. FIG. 8 is displayed, for example, on image screen 74. In one embodiment, display 90 includes a schematic vessel outline 92 and identifies an area within the vessel that is safe for navigation as green, and an unsafe area for navigation as red. The size of the safe and unsafe areas for navigation change as the guide wire is advanced. Thus, as the guide wire is advanced, visual graphic display 90 is dynamically updated to show the changes in the sizes of the safe areas and the unsafe areas. Of course, alternative embodiments include those which use alternate color schemes or indicators for the safe and unsafe areas of navigation in the vessel. In one embodiment, both the vessel image from the interferometric information, and the blood flow information resulting from Doppler shift analysis, are displayed to the operator in a visual graphic display.

In use and referring again to FIG. 1, guide wire assembly 20 is inserted into blood vessel 24, using catheter 26, so that guide wire second end 32 and first optic fiber second end 66 are positioned within blood vessel 24, and second optic fiber second end 70 is positioned outside blood vessel 24, and outside the body.

Light beam source 46 transmits a first light beam to beam splitter 40, which splits the first light beam into second and third substantially equal light beams A and B, respectively. Second light beam A is then transmitted through first optic fiber 42 and third light beam B is transmitted through second optic fiber 44. Second light beam A exits from first optic fiber second end 66 substantially coaxially with respect to guide wire head 32, is at least partially reflected by the tissue, re-enters first optic fiber second end 66 and propagates toward first optic fiber first end 64. Similarly, third light beam B transmitted through second optic fiber 44 is at least partially reflected by reflector 72, re-enters second optic fiber second end 70 and propagates toward second optic fiber first end 68. Light beams A and B are recombined at beam splitter and directed to photodetector 52, including circuit 80.

Upon recombining at beam splitter 40, light beams A and B interfere constructively or destructively with each other depending on the relative lengths of their optical paths and the coherence function of source 46. The optical path length of light beam A depends on the length of first optic fiber 42 and the distance of the reflecting tissue within the blood vessel from first optic fiber first end 66. The optical path length of light beam B depends on the length of second optic fiber 44. For example, when light beam A travels an optical path equivalent in length to the optical path length traveled by light beam B, the two light beams exhibit maximum constructive interference when recombined at beam splitter 40. Similarly, constructive interference can be eliminated by changing the relative optical path lengths of light beams A and B, by enabling PZT's 48 and 50 and stretching the optic fibers. Specifically, out-of-phase voltage signals are applied to PZT's 48 and 50, causing PZT's 48 and 50 to alternately expand and contract and thereby increase and decrease the optical distances along the optic fibers. In particular, alternating between increasing the optical distance along first optic fiber 42, and increasing the optical distance along second optic fiber 44, shifts the interference point of the reflected light beams A and B.

The pattern of interference as the voltage signal is applied to the PZT's 48 and 50 is processed to provide interference points to provide the operator with information to determine if guide wire 28 can be safely advanced. To obtain the interference data, detecting element 52 first detects the light interference patterns or interferences, between the reflected first light beam A and reflected second light beam B, and transmits interference data representative of such interferences to computer 54.

As shown in FIG. 7, interference data, plotted as intensity of reflected light versus distance, is determined by the guide wire guiding apparatus, and computer 54 utilizes the interference data to determine the safety of advancing guide wire 28. For example, computer 54 is programmed with a simple algorithm, using a sliding average of multiple points along the function shown in FIG. 7, to identify true inflection points in the plot of intensity of reflected light versus distance. True inflection points are associated with changes in tissue type, as previously described. In one alternative, if detecting element 52 generates interference data representative of a loss of signal through first optic fiber 42, the optical path lengths along first and second optic fibers 42 and 44 may be varied by expanding PZTs 48 and 50 to reestablish a signal at a new distance from first optic fiber second end 66.

In parallel with, in other words simultaneous with, determination of the intensity of the interference patterns as described above, the Doppler shift in the frequency of the interference patterns is also measured. More specifically, the signal applied to the PZT's is the same for producing both the interferometric information and the Doppler shift information. However, the interferometric information and Doppler shift information are paced by different processes of data extraction and analysis. The Doppler shift information is used to determine the presence of neovascular channels through a vascular obstruction or occlusion. If the presence of neovascular channels is established by reference to the Doppler shift analysis, that information is used by the operator to decide upon a path for navigating the guide wire through the obstruction.

More specifically, a method for determining neovascular flow in a vessel includes generally the step of performing a Doppler shift analysis on the frequencies of interference fringes generated by an interferometric system examining the vessel. Performing the Doppler shift analysis includes the step of applying a known amplitude-modulated voltage signal to PZT's 48 and 50. The vessel tissue is, for example, continually scanned with the frequency modulated signal. Applying the known amplitude-modulated voltage signal to the PZT's results in changing in a known way the optical path-lengths of the light beams as they travel along first optic fiber 42 and second optic fiber 44, resulting in a Doppler shift of the light. The method thus includes the step of calculating or determining an expected Doppler frequency shift due to the known change in optical path-lengths. To obtain the actual Doppler shift, the method includes the step of measuring the actual resulting frequencies of the interference peaks, with circuit 80.

The frequency measurements reveal the actual Doppler shift that consists of two components. A first, known component results from the known change in the optical pathlengths of the light beams with the known amplitude-modulated voltage signal to the PZT's. A second, variable component results from velocity changes of the reflecting target (i.e., red blood cells). The second component of the Doppler shift reveals the presence of neovascular channels. More specifically, the presence of neovascular channels is revealed when the second component of the Doppler shift increases in magnitude, because the velocity of red blood cells is greater than the surrounding tissue of the obstruction or occlusion. To detect the presence of neovascular flow, the method includes the step of subtracting the first, known component of the actual Doppler shift from the actual Doppler shift as measured above. The remainder is due to the second shift component which indicates the presence of neovascular channels. When the presence of neovascular channels through an obstruction is thus established, the operator of the guide wire guiding uses that information to choose a path of least or reduced resistance for advancement of the guide wire. Thus the Doppler shift information is used to guide the guide wire through an obstruction or occlusion within a vessel being examined. In one embodiment, enunciators such as audible tones or visual graphical displays on visual monitors alert the operator, or indicate for the operator, areas of blood flow revealing the presence of neurovascular channels.

Alternative embodiments of the guide wire apparatus are contemplated. In one embodiment, the PZT has a diameter of two inches, and each wrap of an optic fiber around a PZT stretches the optic fiber approximately 10 microns. When the PZT is expanded in response to an applied voltage signal of about 1 kV or below, 150 wraps of the optic fiber around the PZT provide a working viewing range of approximately 1 millimeter. The combined working viewing range of PZTs 48 and 50 connected in reverse parallel configuration provide a working viewing range of about 2 mm. In another embodiment, each optic fiber is wrapped around a PZT 1000 times, thereby providing a range of approximately 5 millimeters of viewing distance. For example, interference points are determined at each of several points at different distances from first optic fiber second end 66, within approximately 5 millimeters, thereby providing the data for approximately 5 millimeters in front of second end 66. The first and second fibers 42 and 44 may be stretched other amounts, to obtain the desired distance.

In one embodiment, computer 54 generates both interferometric and Doppler shift information from the tissue and displays a representative pseudo image on screen 74. Particularly, computer 54 utilizes the interference data generated at various points in the tissue to generate image data representative of a substantially linear image profile of the examined tissue. The Doppler shift information is used to identify neovascular flow through an obstruction in the path of the guide wire, so that the operator can choose a suitable path for advancing the guide through the obstruction. Computer 54 also utilizes the interference data and Doppler shift information to generate and transmit control signals to a monitor while an operator guides guide wire 28 by hand. Alternatively, the control signals may be transmitted to a control device attached to guide wire 28.

The above described guide wire provides a guidance system to determine the safety of advancing the guide wire further into the vessel. The guide wire also provides information to help an operator distinguish among the types of obstructions which might be obstructing advancement of the guide wire. The guide wire also identifies the presence of neovascular channels through an obstruction to aid the operator in establishing a path for the guide wire through the obstruction. However, it is to be understood that the above described guide wire is exemplary and other embodiments are possible. For example, in another embodiment, the guide wire is made with a harder and less floppy end (for example, made of hardened steel) to make it more suitable to go through a partially occluded artery. Such an embodiment is especially suitable for guiding the guide wire through an obstruction in which neovascular channels have been identified as described above. In another alternative embodiment, the guide wire is coated with friction reducing material such as, for example, known polymeric or hydrophilic coating materials. The coating reduces the surface friction to ease advancing the guide wire further into the vessel, and through the obstruction. In another alternative embodiment, the guide wire includes a thin metal wire positioned next to the fiber optic. The thin metal wire is slidably positioned and can be retracted away from the guide wire end, making the guide wire end very floppy. The metal wire, when extended, stiffens the more distal portion of the guide wire.

While the invention has been described in terms of various specific embodiments, those skilled in the art will recognize that the invention can be practiced with modification within the spirit and scope of the claims.

What is claimed is:

1. Apparatus configured to guide a guide wire through body tissue, said apparatus comprising:
   a guide wire having a first proximal end and second distal end; and
   at least one interferometric guidance system comprising:
      a first optic fiber comprising a first end and a second end, said second end coupled to and extending beyond said guide wire distal end; and
   a circuit for generating Doppler shift information relating to neovascular flow through the tissue by revealing relative changes in blood flow velocity at the said second end of said first optic fiber, said interferometric guidance system configured for generating interference information from body tissue.

2. Guide wire guiding apparatus in accordance with claim 1 wherein said interferometric system further comprises:
   a low coherence illumination source for generating a first light beam;
   a beam splitter for splitting the first light beam into a second light beam and a third light beam;
   second optic fiber having a first end and a second end, said first optic fiber wrapped around a first piezo electric transducer, said second optic fiber wrapped around a second piezo electric transducer, said first optic fiber coupled to the guide wire so that said second end of said first optic fiber is adjacent said second end of said guide wire;
   a fixed reflector on said second optic fiber second end; and
   a detecting element communicatively coupled to said first ends of said first and second optic fibers, said detecting element configured to determine interference between a light beam reflected through said first optic fiber and a light beam reflected through said second optic fiber.

3. Guide wire guiding apparatus in accordance with claim 2 wherein said low coherence illumination source comprises a laser.

4. Guide wire guiding apparatus in accordance with claim 2 wherein said low coherence illumination source comprises a superluminescent emitting diode.

5. Guide wire guiding apparatus in accordance with claim 2 wherein said circuit for a generating Doppler shift information comprises:
- a broad band filter; and
- a frequency-to-voltage converter coupled in series to said broad band filter, wherein said broad band filter is coupled to an output of said detecting element.

6. Guide wire guiding apparatus in accordance with claim 5, wherein said circuit for generating Doppler shift information further comprising an FM detector, said FM detector coupled in series to an output of said broad band filter, and to an input of said frequency-to-voltage converter.

7. Guide wire guiding apparatus in accordance with claim 1 wherein said second end of said first optic fiber is polished flat.

8. Guide wire guiding apparatus in accordance with claim 1 wherein said second end of said first optic fiber is polished at an angle of about 8 degrees relative to a cross-sectional plane orthonormal to a long axis of said first optic fiber.

9. Guide wire guiding apparatus in accordance with claim 2 wherein said second optic fiber second end is polished flat.

10. Guide wire guiding apparatus in accordance with claim 2 wherein said second optic fiber second end is polished at an angle of about 8 degrees relative to a cross-sectional plane orthonormal to a long axis of said first optic fiber.

11. Guide wire guiding apparatus in accordance with claim 1 further comprising a visual graphic display coupled to said interferometric system, said visual graphic display configured to display the interferometric information and the Doppler shift information.

12. Apparatus for detecting neovascular flow through an obstruction in a blood vessel, said apparatus comprising:
- a guide wire having a first proximal end and second distal end;
- at least one interferometric guidance system comprising a fiber coupled to and extending beyond said guide wire distal end;
- an interferometric apparatus coupled to said guide wire proximal end and configured to receive data relating to neovascular flow from said fiber;
- a broad band filter coupled to an output of said interferometric apparatus, said interferometric apparatus generating interferometric peaks of varying frequencies; and
- a frequency-to-voltage converter coupled in series to said broad band filter.

13. Apparatus in accordance with claim 12 further comprising an FM detector coupled to an output of said broad band filter and providing an input to said frequency-to-voltage converter.

14. A method to determine neovascular flow through tissue in a vessel, said method comprising:
- using an apparatus configured to guide a guide wire through body tissue which comprises a guide wire having a first proximal end and second distal end, and at least one interferometric guidance system comprising at least one stationary optical fiber coupled to and extending beyond the guide wire distal end;
- examining the vessel with the interferometric system; and
- performing a Doppler shift analysis on frequencies of interference peaks generated by the interferometric system examining the vessel to determine the velocity of blood.

15. A method in accordance with claim 14 wherein performing the Doppler shift analysis includes the steps of:
- applying a known amplitude-modulated voltage signal to a first PZT and a second PZT to produce a first known component of a Doppler frequency shift in the frequencies of interference peaks;
- measuring an actual Doppler frequency shift in the interference peaks;
- subtracting the first known component of the Doppler frequency shift from the actual Doppler frequency shift to determine a second component of the actual Doppler frequency shift, wherein the second component reveals the presence of neovascular channels in the vessel.

16. A method in accordance with claim 15 wherein subtracting the first known component from the actual Doppler frequency shift to determine a second known component comprises the step of determining whether the second component has an increase in magnitude.

17. A method in accordance with claim 14 wherein performing a Doppler shift analysis comprises comparing an actual shift to a predicted shift of the path length change velocity whereby the velocity path component is constant and the observed variance is from a velocity change of the sample component.

18. A method in accordance with claim 14 wherein the neovascular flow is determined by linear changes in the path length of a signal generated by the interferometric system.

* * * * *